US006677482B2

(12) United States Patent
Nishimura et al.

(10) Patent No.: US 6,677,482 B2
(45) Date of Patent: Jan. 13, 2004

(54) METHOD OF MANUFACTURING (METH) ACRYLIC ACID

(75) Inventors: Takeshi Nishimura, Himeji (JP); Yukihiro Matsumoto, Kobe (JP)

(73) Assignee: Nippon Shokubai Co, Ltd., Osaka (JP)

( * ) Notice: Subject to any disclaimer, the term of this patent is extended or adjusted under 35 U.S.C. 154(b) by 0 days.

(21) Appl. No.: 10/326,189

(22) Filed: Dec. 20, 2002

(65) Prior Publication Data

US 2003/0092938 A1 May 15, 2003

Related U.S. Application Data

(62) Division of application No. 09/588,834, filed on Jun. 7, 2000, now Pat. No. 6,525,216.

(30) Foreign Application Priority Data

Jun. 10, 1999 (JP) ............................................. 11-163233

(51) Int. Cl.$^7$ .......................... C07C 51/42; C07C 51/16
(52) U.S. Cl. .................... 562/542; 562/600; 562/512.2; 422/188; 422/198
(58) Field of Search ................................ 262/542, 600, 262/512.2; 422/188, 198

(56) References Cited

U.S. PATENT DOCUMENTS

| | | | |
|---|---|---|---|
| 3,798,264 A | 3/1974 | Kubota et al. | 260/526 N |
| 3,868,417 A | 2/1975 | Duembgen et al. | 260/526 N |
| 4,319,964 A | 3/1982 | Katz et al. | 202/172 |
| 5,705,688 A | 1/1998 | Fauconet et al. | 562/600 |
| 5,785,821 A | 7/1998 | Sakamoto et al. | 230/57 |
| 5,831,124 A | 11/1998 | Machhammer et al. | 562/600 |
| 6,399,817 B1 * | 6/2002 | Chapman et al. | 562/545 |

FOREIGN PATENT DOCUMENTS

| | | |
|---|---|---|
| JP | 53015314 A | 2/1978 |

* cited by examiner

Primary Examiner—Peter O'Sullivan
(74) Attorney, Agent, or Firm—Edwards & Angell, LLP; David G. Conlin; George W. Hartnell, III

(57) ABSTRACT

A method of manufacturing (meth)acrylic acid includes:
  a reaction step of carrying out a catalytic gas-phase oxidation reaction;
  an absorbing step of absorbing (meth)acrylic acid from a (meth)acrylic-acid-containing mixed gas prepared in the reaction step;
  a refinement step of separating, refining, and recovering (meth)acrylic acid from a (meth)acrylic-acid-containing liquid prepared in the absorbing step; and
  a recirculation step of recirculating (meth)acrylic acid contained in a vent gas produced in the refinement step to the absorbing step and/or the refinement step.

10 Claims, 4 Drawing Sheets

METHOD OF MANUFACTURING (METH)ACRYLIC ACID

CROSS-REFERENCE TO RELATED APPLICATIONS

This application is a divisional of co-pending U.S. application Ser. No. 09/588,834 filed Jun. 7, 2000, now U.S. Pat. No. 6,525,216 the teachings of which are incorporated herein by reference, and, which, further, claims priority to Japanese patent application 11-163233 filed Jun. 10, 1999, the teachings of which also are incorporated herein by reference.

FIELD OF THE INVENTION

The present invention relates to a method of manufacturing (meth)acrylic acid.

BACKGROUND OF THE INVENTION

Commercially available (meth)acrylic acid products are manufactured by a manufacturing process that includes a series of a reaction step, an absorbing step, and a refinement step. Specifically, a (meth)acrylic-acid-containing mixed gas prepared by a catalytic gas-phase oxidation reaction in a reactor is introduced to an absorbing column, where (meth)acrylic acid is absorbed using a solvent, such as water. The collected liquid absorbing (meth)acrylic acid is introduced to a refinement step involving various distillation columns in which the (meth)acrylic acid is separated and refined to complete the commercial manufacture of (meth)acrylic acid products.

Here, in the refinement step, a vacuum generator such as an ejector is provided in some kinds of distillation columns used, so as to maintain the interior of the distillation column in vacuum during distillation. As a result, the distillation columns involved in the refinement step produce (meth)acrylic acid, and at the same time discharge a vent gas, that is, a gas containing molecular oxygen introduced for the purpose of inhibiting (meth)acrylic acid from polymerizing.

For these reasons, the vent gas discharged from the distillation columns and their peripherals, including heat exchangers, tanks, and vacuum generators involved in the refinement step, inevitably contain (meth)acrylic acid corresponding to the vapor pressure at a condensation temperature.

Conventionally, the (meth)acrylic acid contained in the vent gas dissolved in a solvent, normally water, used in the ejector was discharged (discarded) in the form of waste water, and the rest in the form of waste gas.

There are other sources for vent gas, including columns and storage tanks (for example, a refined (meth)acrylic acid product storage tank as a product storage tank) used in the absorbing and later steps during which the apparatus is operated at atmospheric or slightly increased pressure. The vent gas from these sources also contain (meth)acrylic acid. Conventionally, the vent gas was, typically, released into the air.

However, as mentioned in the foregoing, the vent gas discharged in the refinement step of manufacture of (meth)acrylic acid contains (meth)acrylic acid. The vent gas, if released into the air or discharged in the form of waste water without being treated, results in a waste of (meth)acrylic acid and reduced yields of (meth)acrylic acid products, and obviously is a cause for environmental pollution too.

SUMMARY OF THE INVENTION

Accordingly, the present invention has objects to improve the yields of (meth)acrylic acid products and also eliminate a cause for environmental pollution by efficiently recovering the (meth)acrylic acid contained in the vent gas produced in the refinement step of a (meth)acrylic acid manufacturing process.

In order to accomplish the objects, the inventors of the present invention have diligently conducted researches, and as a result, found that if the (meth)acrylic-acid-containing vent gas produced in the refinement step is recirculated to the absorbing or later step either with no treatment or after condensing the (meth)acrylic acid contained in the vent gas, the (meth)acrylic acid contained in the vent gas is efficiently recovered and also that if the (meth)acrylic acid contained in the vent gas is recirculated, polymers are reduced in the columns used in the absorbing and later steps. The inventors further found that as a result of the foregoing recirculation, the yields of (meth)acrylic acid products are improved, the manufacturing cost of (meth)acrylic acid products is reduced, and a cause for environmental pollution can be eliminated, which has led to the completion of the invention.

In other words, in order to accomplish the objects, the method of manufacturing (meth)acrylic acid in accordance with the present invention is characterized in that it is a method of manufacturing (meth)acrylic acid by a process constituted by a reaction step, an absorbing step, and a refinement step, wherein the (meth)acrylic acid in the vent gas produced in the refinement step is recirculated in the absorbing or later step, that is, in the absorbing step and/or in the refinement step.

According to the foregoing method, the (meth)acrylic acid in the vent gas produced in the refinement step can be efficiently recovered. Further, by recirculating the (meth)acrylic acid contained in the vent gas, polymers are reduced in those absorbing and distillation columns used in the absorbing and refinement steps. Therefore, the yield of (meth)acrylic acid improves, and the manufacturing cost decreases.

In addition, since the (meth)acrylic acid is efficiently recovered, a cause for environmental pollution can be eliminated.

Additional objects, advantages and novel features of the invention will be set forth in part in the description which follows, and in part will become apparent to those skilled in the art upon examination of the following or may be learned by practice of the invention. The objects and advantages of the invention will become more fully understood from the detailed description given hereinbelow and the accompanying drawings.

DESCRIPTION OF THE EMBODIMENTS

Figure 1:
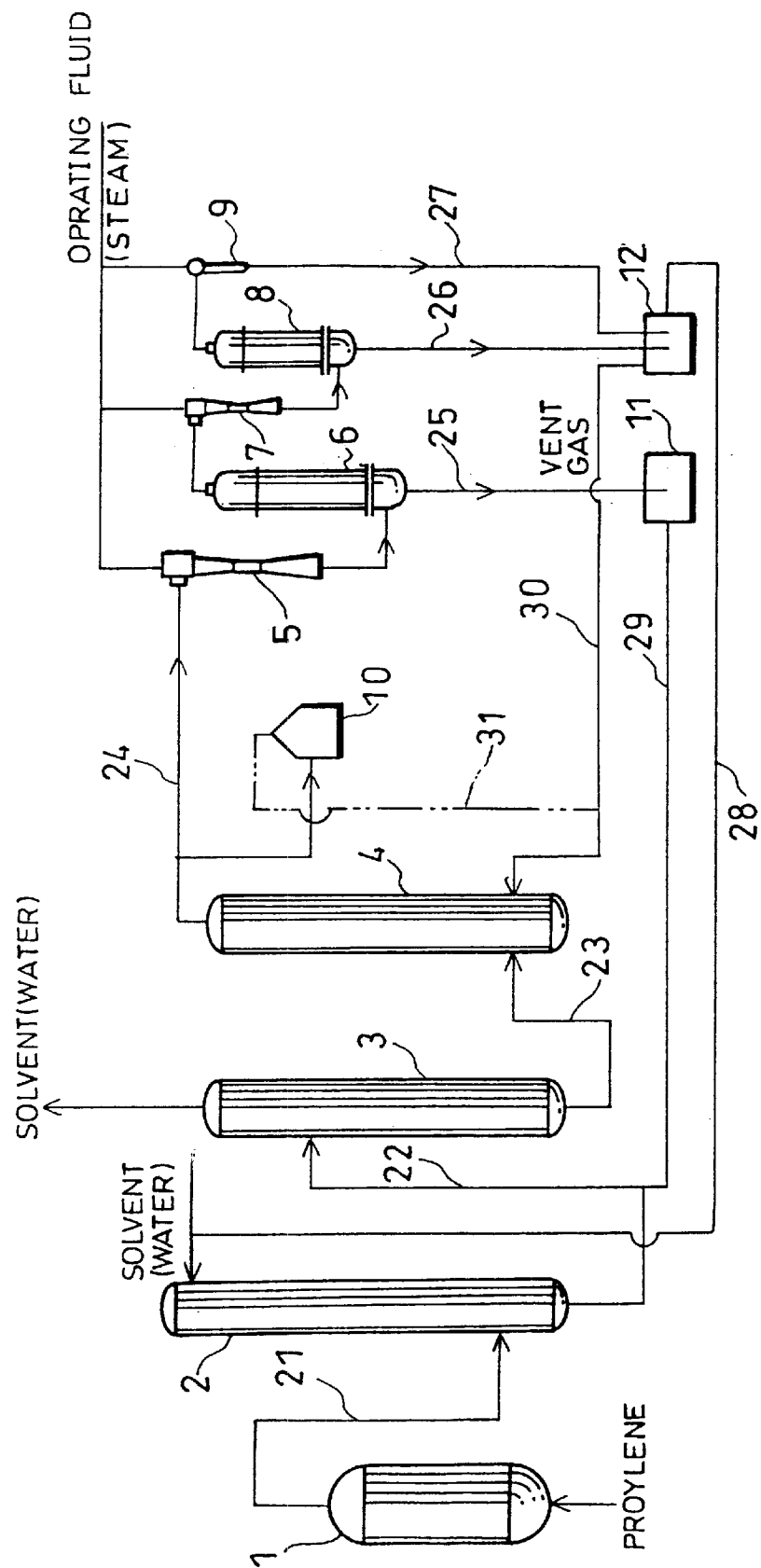
FIG. 1 is an explanatory diagram showing an embodiment in accordance with the present invention.

The method of manufacturing (meth)acrylic acid in accordance with the present invention is a method of manufacturing (meth)acrylic acid by a process constituted by a reaction step, an absorbing step, and a refinements step, wherein the (meth)acrylic acid contained in the vent gas produced in the refinement step is recirculated to the absorbing step and/or a later step.

The method of manufacturing (meth)acrylic acid in accordance with the present invention is, more specifically, constituted by:

a reaction step whereby a catalytic gas-phase oxidation reaction takes place, for example, propylene is subjected to a catalytic gas-phase oxidation reaction;

an absorbing step whereby (meth)acrylic acid is absorbed from a mixed reaction gas ((meth)acrylic-acid-containing mixed gas) obtained in the reaction step by introducing the mixed reaction gas into an absorbing column and dissolving the (meth)acrylic acid in a solvent;

a refinement step whereby (meth)acrylic acid is recovered and refined by separating (meth)acrylic acid from a (meth)acrylic-acid-containing liquid obtained in the absorbing step; and a recirculation step whereby the (meth)acrylic acid contained in the vent gas produced in the refinement step is recirculated to the absorbing step and/or the refinement step.

The refinement step refers collectively to steps subsequent to the absorbing step, ranging from the separation and/or refinement of (meth)acrylic acid to the recovery of (meth)acrylic acid as commercial products, i.e., refined (meth)acrylic acid products (including glacial (meth)acrylic acid): for example, a step of preparing a crude (meth)acrylic acid by separating the solvent from the (meth)acrylic-acid-containing liquid obtained in the absorbing step, and a step of recovering the crude (meth)acrylic acid through refinement. The refinement step may further include, if so desired, for example, a step of separating high boiling point substances (high boiling point components) with high boiling points from (meth)acrylic acid by distilling a crude (meth)acrylic acid, and a step of separating refined (meth)acrylic acid products (i.e., glacial (meth)acrylic acid as commercial products) from low boiling point substances (low boiling point components) with lower boiling points than that of (meth)acrylic acid, for example, by distilling the crude (meth)acrylic acid from which high boiling point substances have been already separated.

In the refinement step, the separation and/or refinement of (meth)acrylic acid may be carried out in vacuum or at atmospheric pressure. Typically, it is carried out in vacuum at low temperatures to inhibit polymerization.

Accordingly, the vent gas produced in the refinement step refers to (meth)acrylic-acid-containing gas produced in the whole course of the refinement step of the (meth)acrylic-acid-manufacturing process, and includes (meth)acrylic-acid-containing vent gases (waste gases) produced in all devices necessarily used for the separation, refinement, and/or recovery of (meth)acrylic acid: namely, vent gases produced in distillation columns at atmospheric pressure or in vacuum; vent gases produced in peripheral devices, such as intermediate storage vessels (tanks), heat exchangers, and vacuum generators, provided as necessary in a solvent separation step, a high boiling point substance separation step, a low boiling point substance separation step, and other steps in the refinement step; vent gases produced in refined (meth)acrylic acid product storage vessels (tanks) as product storage vessels; etc.

In the recirculation step, the (meth)acrylic acid contained in the vent gases is recirculated to the absorbing step and/or the refinement step either with no treatment or after condensing the (meth)acrylic acid contained in the vent gases, the vent gases being produced in all devices necessarily used for the separation, refinement, and/or recovery of (meth)acrylic acid in the refinement step of (meth)acrylic acid.

The following description will discuss in more detail the method of manufacturing (meth)acrylic acid in accordance with the present invention, especially, the recovery and related operations on (meth)acrylic acid in reference to drawings, by taking acrylic acid as an example.

Note although in the following description the focus will be on explanation of the manufacture of acrylic acid, the methods and devices laid out in the following can be utilized readily for the manufacture of methacrylic acid by suitably replacing raw materials with no modification or changes in conditions.

[Embodiment 1]

Referring to FIG. 1, the following will discuss the present embodiment. FIG. 1 is an explanatory diagram showing processing of propylene by catalytic gas-phase oxidation to manufacture acrylic acid, whereby the acrylic acid contained in the vent gas produced in a vacuum distillation column in the refinement step is recirculated to the absorbing step and/or the refinement step. More specifically, FIG. 1 is an explanatory diagram showing an example of condensation of the acrylic acid contained in the vent gas produced in a vacuum distillation column and recirculating into an absorbing column and/or a solvent separation column, and also showing an example of recirculation of the vent gas produced in the course of the condensation of the acrylic acid contained in the vent gas produced in the vacuum distillation column back to the vacuum distillation column, together with the vent gas produced from the aqueous solution of acrylic acid resulting from condensation of the acrylic acid contained in the vent gas produced in the vacuum distillation.

The apparatus for manufacturing acrylic acid (acrylic acid recovery system) used in the present embodiment includes:

a reactor 1 for carrying out a catalytic gas-phase oxidation reaction;

an acrylic acid absorbing column (absorbing column) 2 for absorbing acrylic acid as an acrylic-acid-containing liquid, for example, an aqueous solution of acrylic acid, from the mixed reaction gas by causing a solvent to absorb the mixed reaction gas (acrylic-acid-containing mixed gas) prepared in the reactor 1;

a distillation column 3 as a solvent separation column, disposed downstream of the acrylic acid absorbing column 2, for separating the solvent from the bottom liquid produced in the acrylic acid absorbing column 2 to prepare a crude acrylic acid;

a distillation column (vacuum distillation column) 4 as a fractionating column for fractionating the crude acrylic acid prepared in the distillation column 3;

a vacuum generator for maintaining the distillation column 4 in vacuum and condensing the acrylic acid contained in the vent gas produced in the distillation column 4, the vacuum generator including a first-stage ejector 5, a first-stage condenser 6, a second-stage ejector 7, a second-stage condenser 8, and a third-stage ejector 9;

recirculation lines 28, 29, and 30 as selective recirculation paths extending from the acrylic acid contained in the vent gas produced in the distillation column 4 via the vacuum generator to the acrylic acid absorbing column 2, the distillation column 3, and the distillation column 4; and a refined acrylic acid product storage vessel (tank) 10 as a product storage vessel for recovering and storing, as commercial products, the acrylic acid prepared in the distillation column 4.

The distillation column 4 has peripheral heat exchangers (not shown) including a reboiler and a condenser. Downstream of the condenser is disposed the vacuum generator constituted by the first-stage ejector 5, the first-stage condenser 6, the second-stage ejector 7, the second-stage condenser 8, and the third-stage ejector 9.

In the present embodiment, in the recirculation step, the condensers (the first-stage condenser 6 and the second-stage condenser 8) are arranged so as to condense the vent gas produced in the distillation column 4 and thereby condense the acrylic acid contained in the vent gas, for the purpose of condensing and recirculating the acrylic acid contained in the vent gas.

Further downstream of the vacuum generator are disposed the tanks (intermediate storage tanks) 11 and 12 for recovering and temporarily storing the condensate containing the acrylic acid (for example, aqueous solution of acrylic acid) prepared in the vacuum generator. Further downstream of the tanks 11 and 12 are disposed the recirculation lines 28, 29, and 30 for recirculating the acrylic acid contained in the vent gas produced in the distillation column 4 via the vacuum generator to the acrylic acid absorbing column 2, the distillation column 3, and the distillation column 4 respectively. Thus, the acrylic acid condensed in the condenser is recirculated to the absorbing step and a later step.

Now, the following description will discuss a method of manufacturing acrylic acid (method of recovering acrylic acid) using the foregoing apparatus for manufacturing acrylic acid (acrylic acid recovering system).

First, referring to FIG. 1, propylene is introduced to the reactor 1 so as to subject it to a catalytic gas-phase oxidation reaction therein (reaction step). As shown in FIG. 1, the reactor 1 is capable of solely performing preceding and subsequent reactions. In some cases, however, separate reactors may be used to perform the preceding reaction to produce acrolein from propylene and the subsequent reaction to produce acrylic acid from the acrolein respectively, with the gas produced in the preceding reactor being introduced to the subsequent reactor with or without additional air, steam, and the like.

The mixed reaction gas (acrylic-acid-containing mixed gas) prepared in the reactor 1 is introduced via a path 21 into the acrylic acid absorbing column 2. In the acrylic acid absorbing column 2, acrylic acid is absorbed (absorbing step) by causing a solvent, normally water, to contact the acrylic-acid-containing mixed gas prepared in the reactor 1, so as to form a solution of acrylic acid (here, aqueous solution of acrylic acid).

Subsequently, the aqueous solution of acrylic acid prepared in the absorbing step is transported through a path 22 for a refinement step. In the refinement step, first, water is separated in the distillation column 3, whilst a crude acrylic acid appears as a bottom liquid at the bottom of the distillation column 3. Then, the crude acrylic acid is introduced via a path 23 into the distillation column 4 to be fractionated by the vacuum generator in vacuum.

The acrylic acid fractionated in the distillation column 4 is recovered and stored in the refined acrylic acid product storage tank 10.

Meanwhile, the vent gas produced in the distillation column 4 is introduced via a path 24 into the vacuum generator where the vent gas contacts steam as an operating fluid via the first-stage ejector (steam ejector) 5. The vent gas is then liquified as a result of condensation in the first-stage condenser 6. As the acrylic acid contained in the vent gas produced in the distillation column 4 is condensed, the condensate in the first-stage condenser 6 is recovered via a path 25 in the tank 11 as an aqueous solution of acrylic acid.

The vent gases produced in the first-stage ejector 5 and the first-stage condenser 6 contact steam as an operating fluid via the second-stage ejector (steam ejector) 7 and liquified as a result of condensation in the second-stage condenser 8. The condensate (aqueous solution of acrylic acid) in the second-stage condenser 8 is recovered through a path 26 to the tank 12, and mixed with water containing the vent gases which have been produced in the second-stage ejector 7 and the second-stage condenser 8 and then recovered from the third-stage ejector (steam ejector) 9 via a path 27 into the tank 12.

The acrylic acid concentration in the mixture stored in the tank 12 is low, compared to the acrylic acid concentration in the condensate produced in the first-stage condenser 6 and stored in the tank 11. Therefore, the mixture in the tank 12 is transported via a recirculation line 28 and fed to the acrylic acid absorbing column 2 together with a solvent, such as, water, for absorbing acrylic acid. The mixture then once again undergoes the absorbing step before going through the refinement step.

Meanwhile, the condensate from the first-stage condenser 6 is transported via the tank 11 and the recirculation line 29 and fed to the distillation column 3 together with the bottom liquid produced in the acrylic acid absorbing column 2. The condensate then once again undergoes the refinement step.

The foregoing recirculation of the condensed acrylic acid contained in the vent gas produced in the distillation column 4 to the acrylic acid absorbing column 2 and the distillation column 3 enables efficient recovery and reuse of the acrylic acid contained in vent gases that was conventionally discarded, and results in improved yields of acrylic acid products.

Further, the vent gases from the ejectors (the first-stage ejector 5, the second-stage ejector 7, and the third-stage ejector 9) typically contain molecular oxygen introduced to inhibit polymerization in distillation columns (for example, the distillation columns 3 and 4). Therefore, the vent gases produced in those ejectors are partly or entirely recirculated to the distillation column to reuse the molecular oxygen contained in the vent gases.

In the present embodiment, recirculating the vent gas recovered from the third-stage ejector 9 via the path 27 to the tank 12, together with the vent gas produced from the mixture in the in the tank 12, via the recirculation line 30 to the distillation column 4, enables reuse of the molecular oxygen contained in the vent gas transported from the tank 12 to the distillation column 4 and recovery of the acrylic acid contained in the vent gases through recirculation. However, the vent gas may be recirculated partly or entirely to the distillation column directly from the path 27 without passing through the tank 12 and, in some cases, via a reboiler.

The tanks 11 and 12, as wells as in storage tanks including the refined acrylic acid product storage tank 10, in some cases contain a seal gas of low oxygen gas content, so as to inhibit the polymerization of acrylic acid and to prevent ignition from leading to explosion. This makes it likely for vent gas to be produced.

For these reasons, the recovery and recirculation of the vent gas produced in these storage tanks is instrumental in improving the efficiency in recovering acrylic acid. The foregoing operation is effective in efficiently recovering the acrylic acid contained in vent gas, making use of the acrylic acid contained in vent gas which was conventionally discarded, and improving the yields of acrylic acid products. The recirculation lines 28, 29, and 30 are available for the recirculation of the (meth)acrylic acid in the vent gas produced in these storage tanks. The (meth)acrylic acid in the vent gas produced in these storage tanks can be recirculated after condensing it through contact with a condensate in, for example, a storage tank.

In FIG. 1, the arrangement is such that the vent gas produced in the tank 12 is returned to the distillation column 4. However, an arrangement may be made such that the vent gas produced in the tank 11, as well as the vent gas produced in the tank 12, is returned to the distillation column 4. A further alternative arrangement is possible such that the acrylic acid in the vent gas produced in the refined acrylic acid product storage tank 10 is returned via, for example, the recirculation line 30 to the distillation column 4 if, for example, a recirculation line 31 may be provided as a path represented by alternate long and two short dash lines. Alternatively, the vent gas may be recirculated to the acrylic acid absorbing column 2 by a blower as will be discussed later in an embodiment. Further, a condensate prepared from the condensation of the acrylic acid in the vent gas may be recirculated to the absorbing step and/or the refinement step via the recirculation paths 28 and 29.

In addition to the distillation columns 3 and 4, the apparatus for manufacturing acrylic acid shown in FIG. 1 may include more devices in the refinement step if necessary: it is obvious, for example, that a low boiling point substance separation column or a high boiling point substance separation column may be provided between the distillation column 3 and the distillation column 4.

In the present embodiment, two separate tanks for recovering condensate are provided so as to suitably handle different acrylic acid densities in the condensates; however, a common single tank may be shared. The recovery of condensate that is suitably adjusted according to the acrylic acid concentration in the condensate enables recirculation of the recovered condensate to the most suitable step (the most suitable column) where the acrylic acid concentration shows the most similar value.

In the present embodiment, among the recovered condensates, the condensate recovered from the first-stage condenser 6 with the higher acrylic acid concentration is returned to the distillation column 3, whilst the condensate recovered from a subsequent condenser (the second-stage condenser 8 in the case of the apparatus for manufacturing acrylic acid shown in FIG. 1) with the lower acrylic acid concentration is returned to the acrylic acid absorbing column 2.

This is due to the following reasons. In the acrylic acid absorbing column 2, acrylic acid is absorbed in a solvent (water in this case) absorbing the acrylic-acid-containing mixed gas prepared in the reactor 1; therefore, to improve the efficiency in absorbent, the solvent used has an acrylic acid concentration that is reduced to the lowest possible level, and preferably does not contain acrylic acid at all. Meanwhile, in the distillation column 3, so as to remove solvent (water in this case) from the solution of acrylic acid (aqueous solution of acrylic acid in this case) to prepare a crude acrylic acid with a high acrylic acid concentration, the non-acrylic-acid component (solvent) preferably makes up a small percentage to attain better efficiency.

For these reasons, acrylic acid is efficiently recoverable when, among the recovered condensates, the condensate with the lower acrylic acid concentration is returned to the acrylic acid absorbing column 2, whilst the condensate with the higher acrylic acid concentration is returned to the distillation column 3.

Further, the foregoing recirculation of the recovered condensate or vent gas to a place (column) in which the liquid or gas has a similar composition to that of the recirculation liquid or gas to be recirculated, in other words, the selection of destination in a recirculation flow depending on the concentration of the recirculated acrylic acid in the recirculation step, is also preferable in view of optimization of the liquid composition in the columns.

Therefore, no particular limitations are imposed on the destination to which the recovered condensate or vent gas is recirculated (returned). Preferably, the recovered condensate or vent gas is recirculated (returned) to a place in which the liquid or gas has a similar composition to that of the recirculation liquid or gas to be recirculated.

For these purposes, the number of stages in the vacuum generator (i.e., the number of ejectors and condensers used) may be specified in design in an arbitrary fashion to some extent according to cost effectiveness and targeted degree of vacuum in relation to the amount of operating fluid (steam) actually used. However, in order to carry out an operation suitable to the acrylic acid concentration in the recovered condensate, two or more stages are preferably provided.

Further, in the present embodiment, a gas, such as molecular oxygen, is used as a polymerization inhibitor to inhibit the polymerization of acrylic acid. The acrylic acid not condensed in the first-stage condenser 6 is discharged and contained in the vent gas together with the molecular oxygen; therefore, the acrylic acid is desirably recovered after being condensed by a condenser, for improvement of the efficiency in recovering acrylic acid. The vent gas produced in the vacuum generator contains the gaseous molecular oxygen introduced as a polymerization inhibitor, and therefore may be recirculated to a distillation column either directly or via a reboiler adjoining to the distillation column. To recover the acrylic acid, the vent gas produced in the vacuum generator may be passed through the vacuum generator again and recirculated. Further, if the solvent is water, the explosive reactivity of the vent gas can be reduced by the diluting effect of the water contained in the recirculated gas.

Further, in FIG. 1, the arrangement is such that the water containing vent gases from the second-stage ejector 7 and the second-stage condenser 8 are directly recovered from the third-stage ejector 9 to the tank 12. Alternatively, the condenser may be connected to the third-stage ejector 9 too.

The condensates prepared in the first-stage condenser 6 and the second-stage condenser 8 do not necessarily recirculated in their entire mass. However, the recirculation in their entire mass is preferable in recovering the acrylic acid contained in vent gas. When this is the case, the tanks 11 and 12 are dispensable with the condensates being directly recirculated from the first-stage condenser 6 and the second-stage condenser 8 to the acrylic acid absorbing column 2 and the distillation column 3.

The foregoing arrangement was such that water was used as a solvent in the acrylic acid absorbing column 2, whilst steam was used as an operating fluid in the vacuum generator; however, these are not the only options available. Alternatively, the solvent and the operating fluid may be any substances as long as they are a solvent and its vapor capable of absorbing the component (acrylic acid in this case) to be recovered. Note that in the present embodiment, the operating fluid is preferably vapor of the solvent used in the acrylic acid absorbing column 2 in order to return the condensate or the mixture obtained via the vacuum generator to the acrylic acid absorbing column 2 as a recirculation liquid.

In the present embodiment, the vacuum generator is supposed to include ejectors and condensers; however, a vacuum pump may be provided so as to replace the ejectors and condensers.

As discussed in detail so far, according to the present embodiment, the (meth)acrylic acid in the vent gas produced in the refinement step is condensed and recirculated as aqueous solution of (meth)acrylic acid as shown in FIG. 1. The solution is an operating fluid (solvent) used in the vacuum generator absorbing and dissolving (meth)acrylic acid.

In other words, in the present embodiment, the recirculation step includes: a step of condensing the vent gas produced in the course of the refinement step, that is, the vent gas produced in the foregoing devices (for example vacuum generator) necessary used for the separation, refinement, and/or recovery of (meth)acrylic acid; and a step of recirculating the (meth)acrylic acid contained in the condensate prepared in this step to a product flow in the absorbing step and/or the refinement step, specifically, to the absorbing column and/or the refinement column (distillation column).

The recirculation step, if necessary, may further include: a step of recovering and storing the condensate prepared in the step of condensing the vent gas produced in the refinement step; and a step of recirculating the vent gas produced from the recover liquid prepared in the foregoing step to a product flow in the refinement step, specifically, to the refiner (distillation column).

According to a variation of the present embodiment, the recirculation step may further include a step of recirculating the vent gas produced in the refinement step to a product flow in the refinement step, specifically, to a refinement column (distillation column), such as the fractionating column.

As discussed in detail so far, the present embodiment is characterized in that the (meth)acrylic acid in the vent gas produced in the refinement step is recirculated to the absorbing step and/or a later step.

Note that although vent gas is produced also in the absorbing step, i.e., in the acrylic acid absorbing column 2, the vent gas discharged here includes large amounts of non-condensing gas which does not condense at normal temperature and which includes large amounts of non-reacted propylene and oxygen. Therefore, the vent gas produced in the absorbing step is preferably recovered and returned to the reaction step, i.e., to the reactor 1. Accordingly, the present embodiment preferably includes such a step in order to efficiently recover (meth)acrylic acid.

What makes the present embodiment stand out as being distinguished over conventional or other technologies is that a special attention is paid to the conventionally discarded (meth)acrylic acid contained in the vent gas produced in the refinement step, and the (meth)acrylic acid in the vent gas is recovered and recirculated. Advantages especially worth mentioning are such that recirculated components (recovered components) are recirculated, depending on recovery methods, to a place (step) which is most suitable to the composition of the recirculated components, that is, a place (step) in which components has a composition most similar to that of the recirculated components, so as to efficiently recover the (meth)acrylic acid in the vent gas produced in the refinement step, and that the recirculation enables a reduction in the amounts of polymers produced in the absorbing column and the distillation column used in the absorbing step and the refinement step. These advantages are available only when the (meth)acrylic acid in the vent gas produced in the refinement step is recirculated to the absorbing step and/or a later step. The mechanism behind the recirculation of the (meth)acrylic acid in the vent gas produced in the refinement step enabling a reduction in the amounts of polymers produced in the absorbing column and the distillation column is not clearly understood. However, it is assumed that the recirculation of the (meth)acrylic acid would optimize the composition of liquid in the columns.

As discussed in detail so far, according to the present embodiment, the (meth)acrylic acid in the vent gas produced in the refinement step is efficiently recovered, and polymers are reduced in the absorbing column and the distillation column used in the absorbing step and the refinement step; therefore, the yields of (meth)acrylic acid improve and manufacturing cost is reduced.

Further, since (meth)acrylic acid is efficiently recovered, a cause for environmental pollution can be eliminated.

[Embodiment 2]

Figure 2:
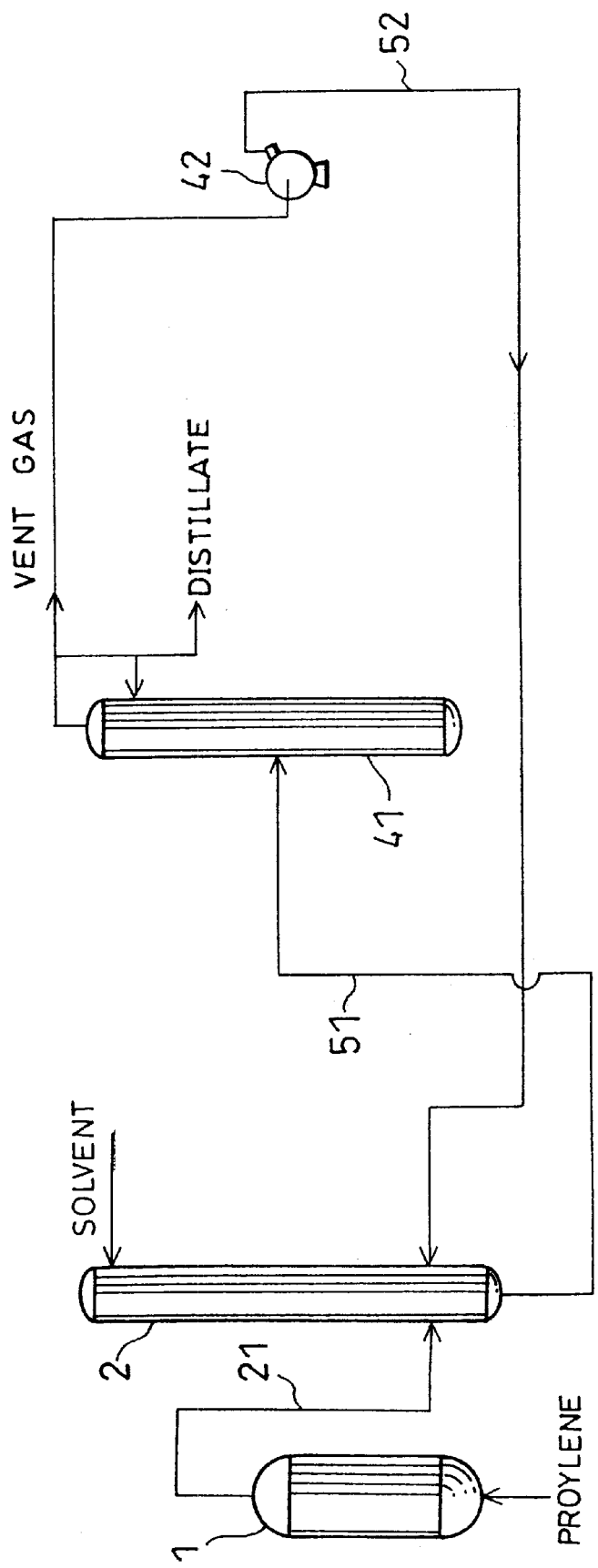
FIG. 2 is an explanatory diagram showing another embodiment in accordance with the present invention.

Referring to FIG. 2, the following description will discuss the present embodiment. The description will primarily focus on the differences of the present embodiment from the first embodiment, and, for convenience, members of the present embodiment that have the same arrangement and function as members of the first embodiment, and that are mentioned in the first embodiment are indicated by the same reference numerals and description thereof is omitted.

FIG. 2 is an explanatory diagram showing processing of propylene by catalytic gas-phase oxidation to manufacture acrylic acid, whereby the acrylic acid contained in the vent gas produced in an atmospheric pressure distillation column in the refinement step is being recirculated and fed to the absorbing step. More specifically, FIG. 2 is an explanatory diagram showing an example of the vent gas produced in atmospheric pressure distillation column is recirculated to an acrylic acid absorbing column.

The apparatus for manufacturing acrylic acid (acrylic acid recovery system) for use in the present embodiment is arranged so as to include an atmospheric pressure distillation column (refinement column) 41, disposed downstream of the acrylic acid absorbing column 2 of the apparatus for manufacturing acrylic acid shown in FIG. 1 in relation to the first embodiment, for separating and refining acrylic acid. The reactor 1 and the acrylic acid absorbing column 2 in the apparatus for manufacturing acrylic acid of FIG. 2 are identical to those of FIG. 1.

A blower 42 as a pressurizer is disposed downstream of the atmospheric pressure distillation column 41 as necessary. A recirculation line 52 is disposed as a path to recirculate the acrylic acid contained in the vent gas produced in the atmospheric pressure distillation column 41 via the blower 42 to the acrylic acid absorbing column 2, replacing the recirculation lines 28, 29, and 30 of the apparatus for manufacturing acrylic acid of FIG. 1.

According to a method of manufacturing acrylic acid (method of recovering acrylic acid) using this apparatus for manufacturing acrylic acid, first, similarly to the foregoing first embodiment, propylene is introduced to the reactor 1 so as to subject it to a catalytic gas-phase oxidation reaction (reaction step). The mixed reaction gas (acrylic-acid-containing mixed gas) prepared in the reactor 1 is introduced to the acrylic acid absorbing column 2 via the path 21. In the acrylic acid absorbing column 2, the acrylic-acid-containing mixed gas prepared in the reactor 1 is brought into contact with a solvent, normally water, so as to absorb acrylic acid as a solution of acrylic acid (for example, aqueous solution of acrylic acid) (absorbing step).

Subsequently, as shown in FIG. 2, the aqueous solution of acrylic acid prepared in the absorbing step is transported from the path 51 via a distillation column (not shown) to the atmospheric pressure distillation column 41 where acrylic acid is refined at atmospheric pressure (refinement step). The distillate is recovered. The vent gas produced in the atmospheric pressure distillation column 41 is preferably pressurized moderately by the blower 42 disposed along the recirculation line 52, then transported to the acrylic acid absorbing column 2, and again subjected to the absorbing step and fed back to the refinement step. The discharge pressure (i.e., pressure to be applied) of the blower 42 is not limited in any particular manner, as long as the vent gas is steadily and surely recirculated to the acrylic acid absorbing column 2.

As discussed in detail so far, according to the present embodiment, the vent gas produced in the refinement step, that is, in the atmospheric pressure distillation column 41 is returned to the acrylic acid absorbing column 2 in the recirculation step, so as to recirculate the acrylic acid contained in the vent gas produced in the refinement step to the absorbing step.

In other words, according to the present embodiment, the recirculation step includes a step of recirculating the vent gas produced in the refinement step to the absorbing step with no treatment, specifically, to the absorbing column. In the present embodiment, vent gas is produced in devices operated atmospheric pressure. The recirculation step is carried out while the pressurizer is applying a pressure as necessary, According to the present embodiment, the vent gas produced in the refinement step is recirculated to the absorbing step, so as to absorb again the (meth)acrylic acid contained in the vent gas in the absorbing column and to feed to the refinement step, Therefore, in the present embodiment also, the (meth)acrylic acid in the vent gas produced in the refinement step can be efficiently recovered. Further, according to the arrangement of the present embodiment, the recirculation of the (meth)acrylic acid in the vent gas produced in the refinement step enables a reduction in the amounts of the polymers produced in the absorbing column and the distillation column. therefore, yields of (meth) acrylic acid improve, manufacturing cost is reduced, and a cause for environmental pollution can be eliminated in the present embodiment similarly to the first embodiment.

Note that in the present embodiment also, the vent gas produced in the absorbing step is preferably recovered and returned to the reaction step, in order to improve the yields of (meth)acrylic acid.

[Embodiment 3]

Figure 3:
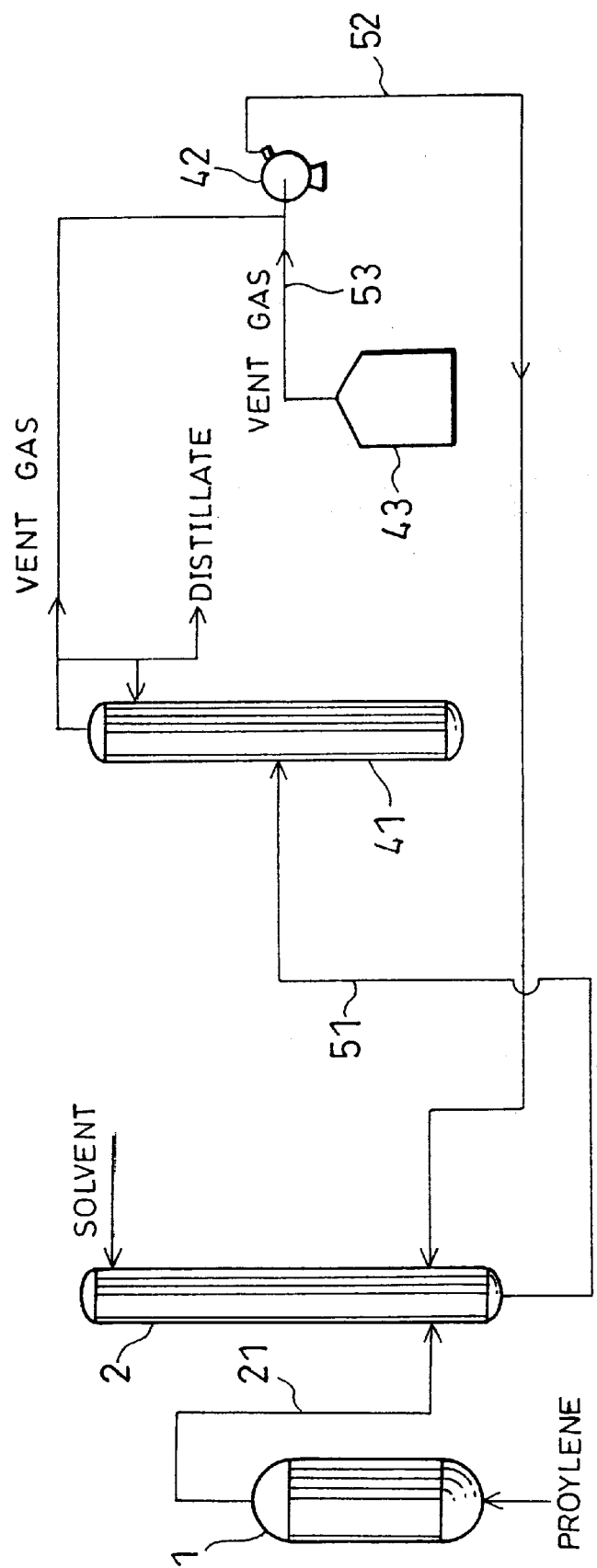
FIG. 3 is an explanatory diagram showing a further embodiment in accordance with the present invention.

Referring to FIG. 3, the following description will discuss the present embodiment. The description will primarily focus on the differences of the present embodiment from the second embodiment, and, for convenience, members of the present embodiment that have the same arrangement and function as members of the first or second embodiment, and that are mentioned in the first or second embodiment are indicated by the same reference numerals and description thereof is omitted.

FIG. 3 is an explanatory diagram showing processing of propylene by catalytic gas-phase oxidation to manufacture acrylic acid, whereby the acrylic acid contained in the vent gas produced in an atmospheric pressure distillation column in the refinement step and the acrylic acid contained in the vent gas produced in a refined acrylic acid product storage tank are recirculated and fed to the absorbing step.

More specifically, FIG. 2 is an explanatory diagram showing an example of recirculation of the vent gas produced in an atmospheric pressure distillation column and the vent gas produced in a refined acrylic acid product storage tank to an acrylic acid absorbing column.

The apparatus for manufacturing acrylic acid (acrylic acid recovery system) of FIG. 3 for use in the present embodiment is basically identical to the apparatus for manufacturing acrylic acid shown in FIG. 2 in relation to the second embodiment, and further includes:

a refined acrylic acid product storage vessel (tank) 43 as a product storage vessel for recovering and temporarily storing acrylic acid products; and a path 53 connected to the recirculation line 52 for recirculating the vent gas produced in the refined acrylic acid product storage vessel 43, as well as the vent gas produced in the atmospheric pressure distillation column (refinement column) 41, via the blower 42 to the acrylic acid absorbing column 2. The reactor 1 and the acrylic acid absorbing column 2 in the apparatus for manufacturing acrylic acid of FIG. 3 are identical to those of FIG. 1 and FIG. 2. Otherwise, the apparatus for manufacturing acrylic acid of FIG. 3 is identical to that of FIG. 2 in arrangement.

A method of manufacturing of acrylic acid (method of recovering acrylic acid) using this apparatus for manufacturing acrylic acid is identical to the second embodiment up to the refinement step. Besides, the method is basically identical to the method of the second embodiment as far as the recirculation flow of the vent gas produced in the atmospheric pressure distillation column 41 is concerned whereby the distillate is recovered, and the vent gas produced in the atmospheric pressure distillation column 41 is preferably pressurized moderately by the blower 42, transported through the recirculation line 52 to the acrylic acid absorbing column 2, and again subjected to the absorbing step and fed to the refinement step; however, in the present embodiment, the vent gas produced in the refined acrylic acid product storage vessel 43 is transported through the path 53 to the recirculation line 52, pressurized moderately by the blower 42 together with the vent gas produced in the atmospheric pressure distillation column 41, transported to the acrylic acid absorbing column 2, and again subjected to the absorbing step and fed to the refinement step.

The refined acrylic acid product storage vessel 43 may be a storage tank for a refined acrylic acid product obtained in the atmospheric pressure distillation column 41, or a storage tank for a refined acrylic acid product recovered from another distillation column (refinement column) such as a fractionating column (not shown) Another possible arrangement is such that the vent gas produced in the refined acrylic acid product storage vessel 43 is recirculated, together with the vent gas produced in the atmospheric pressure distillation column 41, through the recirculation line 52 to the acrylic acid absorbing column 2 as shown in FIG. 3. Alternatively, the acrylic acid and the vent gas may be recirculated through individual recirculation lines (paths) to the acrylic acid absorbing column 2. The acrylic acid and the vent gas are preferably recirculated as the vent gas is pressurized by a pressurizer such as a blower 42, in order to prevent reverse flow and encourage efficient and steady recirculation of the acrylic acid and the vent gas to the acrylic acid absorbing column 2. The provision of a pressurizer is, however, not essential.

As discussed in detail so far, in the present embodiment, similarly to the second embodiment, the vent gas produced in the refinement step is returned to the acrylic acid absorbing column 2 with no treatment so as to recirculate the acrylic acid contained in the vent gas produced in the refinement step to the absorbing step.

In other words, in the present embodiment, the recirculation step includes a step of recirculating the vent gas produced in the refinement step to the absorbing step, specifically, to the absorbing column, whereby the vent gas produced in the refinement step encompasses the vent gas produced in a distillation column (atmospheric pressure distillation column) and/or the vent gas produced from refined and recovered (meth)acrylic acid, i.e., the (meth) acrylic acid stored in the refined product (product) storage tank. Here, the vent gas produced in a distillation column (atmospheric pressure distillation column) and/or the vent gas produced from refined and recovered (meth)acrylic acid are recirculated while being pressurized by a pressurizer if necessary.

The present embodiment includes, in addition to the arrangement of the second embodiment, an arrangement such that the vent gas produced from the (meth)acrylic acid recovered in the refinement step, that is, the vent gas produced in the refined product storage tank, is also recirculated to the absorbing step; therefore, the (meth)acrylic acid contained in the vent gas is absorbed again in the absorbing column, and fed to the refinement step. For these reasons, in the present embodiment, the (meth)acrylic acid in the vent gas produced in the refinement step is more efficiently recovered than in the second embodiment, further improving yields of (meth)acrylic acid, reducing manufacturing cost, and eliminating a cause for environmental pollution.

[Embodiment 4]

Figure 4:
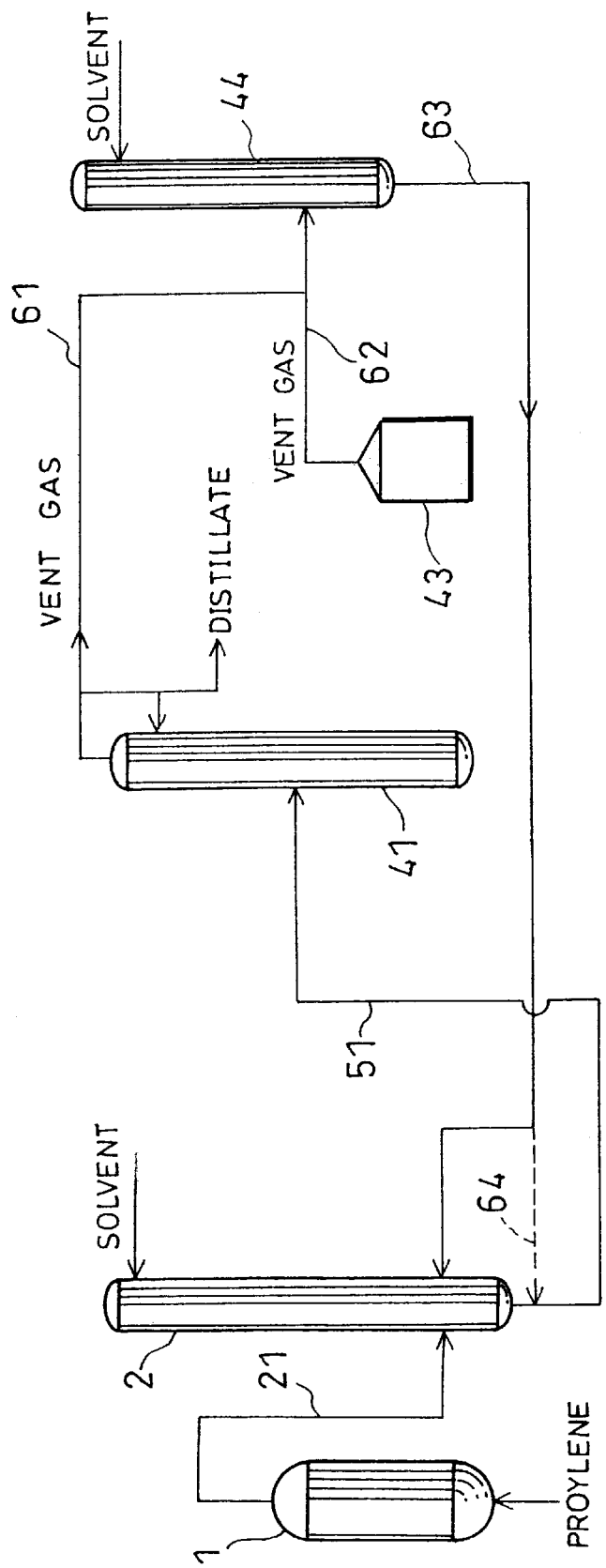
FIG. 4 is an explanatory diagram showing still a further embodiment in accordance with the present invention.

Referring to FIG. 4, the following description will discuss the present embodiment. The description will primarily focus on the differences of the present embodiment from the third embodiment, and, for convenience, members of the present embodiment that have the same arrangement and function as members of the first to third embodiments, and that are mentioned in the first to third embodiments are indicated by the same reference numerals and description thereof is omitted.

FIG. 4 is an explanatory diagram showing processing of propylene by catalytic gas-phase oxidation to manufacture acrylic acid, whereby the acrylic acid contained in the vent gas produced in an atmospheric pressure distillation column in the refinement step and the acrylic acid contained in the vent gas produced in a refined acrylic acid product storage tank is recirculated as a solution of acrylic acid and fed to the absorbing step and/or the refinement step after being absorbed in advance. More specifically, FIG. 4 is an explanatory diagram showing an example of the vent gas produced in an atmospheric pressure distillation column and the vent gas produced in a refined acrylic acid product storage tank partly or entirely being recirculated through an absorption device disposed downstream of an atmospheric pressure distillation column to an acrylic acid absorbing column and/or a distillation column (atmospheric pressure distillation column) disposed upstream of the atmospheric pressure distillation column.

The apparatus for manufacturing acrylic acid (acrylic acid recovery system) for use in the present embodiment is basically identical to the apparatus for manufacturing acrylic acid shown in FIG. 3 in relation to the third embodiment, and further includes:

a vent-gas-dedicated absorption device (second absorbing column) 44, disposed downstream of the atmospheric pressure distillation column (refinement column) 41 and the refined acrylic acid product storage vessel 43 so as to replace the blower 42, for partly or entirely absorbing the vent gas produced in the atmospheric pressure distillation column 41 that is a refinement column and the vent gas produced in the refined acrylic acid product storage vessel 43; and recirculation lines 63 and 64 as paths for recirculating the absorbent (solution of acrylic acid) prepared in the absorption device 44 to the acrylic acid absorbing column 2 and the atmospheric pressure distillation column 41. The reactor 1 and the acrylic acid absorbing column (first absorbing column) 2 of the apparatus for manufacturing acrylic acid shown in FIG. 4 are identical to those shown in FIG. 1 to FIG. 3. Otherwise, the apparatus for manufacturing acrylic acid of FIG. 4 is identical to that of FIG. 3 in arrangement.

A method of manufacturing acrylic acid (method of recovering acrylic acid) using this apparatus for manufacturing acrylic acid is identical to that of the second embodiment 2 up to the refinement step. However, the vent gas produced in the atmospheric pressure distillation column 41 is temporarily transported through the path 61 to the absorption device 44. The vent gas produced in the refined acrylic acid product storage vessel 43 is also temporarily transported through a path 62 to the absorption device 44. In the absorption device 44, the vent gases are brought into contact with a solvent, normally water, to allow the acrylic acid contained in the vent gases to be absorbed (absorbed) in the solvent (water). The resultant solution of acrylic acid (aqueous solution of acrylic acid) is partly or entirely recirculated through the recirculation line 63 to the acrylic acid absorbing column 2. In this case, the solution of acrylic acid prepared in the absorption device 44 may be partly or entirely recirculated through the recirculation line 64 to the atmospheric pressure distillation column 41, together with the bottom liquid (that is, absorbent (solution of acrylic acid)) from the acrylic acid absorbing column 2, as denoted by a dotted line.

The vent-gas-dedicated absorption device 44 for use in the present embodiment is not limited in any particular manner as long as the vent gas can be brought into contact with a solvent to allow acrylic acid to be absorbed in the solvent. For example, the absorption device 44 may be an acrylic acid absorbing column that is identical to the acrylic acid absorbing column 2. The solvent for use in the absorption device 44 is not limited in any particular manner as long as it is capable of absorbing acrylic acid; however, the same type of solvent with the one used in the acrylic acid absorbing column 2 is preferred.

As discussed in detail so far, according to the present embodiment, the vent gas produced in the refinement step, i.e., in the atmospheric pressure distillation column 41 and the refined acrylic acid product storage vessel 43, is absorbed in a solvent in the recirculation step and returned to the acrylic acid absorbing column 2 and/or the atmospheric pressure distillation column 41, so as to recirculate the acrylic acid contained in the vent gas produced in the refinement step to the absorbing step and/or the refinement step as a liquid, specifically, a solution of acrylic acid.

Therefore, in the present embodiment, the recirculation step includes: a step of causing a solvent to absorb a part or the entirety of the vent gas produced in the refinement step to absorb the (meth)acrylic acid contained in the vent gas in advance; and a step of recirculating the bottom liquid (solution of (meth)acrylic acid) prepared in the foregoing step to the absorbing step that precedes the refinement step, that is, the absorbing step whereby the mixed reaction gas (a (meth)acrylic-acid-containing mixed gas) prepared in the reaction step is absorbed, and/or the refinement step, specifically, to the refinement column (distillation column) and/or the absorbing column (first absorbing column) disposed upstream of the refinement column (distillation column).

Therefore, in the present embodiment also, the (meth)acrylic acid in the vent gas produced in the refinement step can be efficiently recovered, the liquid composition is optimized in columns due to the recirculation of (meth)acrylic acid, and polymers are reduced in the absorbing column and the distillation column for use in the absorbing step and the refinement step. Accordingly, the yields of (meth)acrylic acid improve, and manufacturing cost is reduced.

Further, since (meth)acrylic acid is efficiently recovered, a cause for environmental pollution can be eliminated.

Note that in the present embodiment also, the vent gas produced in the absorbing step is preferably recovered and returned to the reaction step, in order to improve the yields of (meth)acrylic acid.

In the following, the present invention will be discussed in further detail by means of examples and comparative examples. However, these examples and comparative examples have illustrative purposes only, and by no means restrict the scope of the present invention.

EXAMPLE 1

According to the process denoted by solid lines in FIG. 1, propylene was subjected to a catalytic gas-phase oxidation reaction in the reactor 1 (reaction step), acrylic acid was absorbed in water in the acrylic acid absorbing column 2 (absorbing step), water was separated from the aqueous solution of acrylic acid (acrylic acid absorbing column bottom liquid) in the distillation column 3, and then crude acrylic acid was refined in the distillation column 4.

The column top of the distillation column 4 was coupled to the vacuum generator which was constituted by the first-stage ejector 5, the first-stage condenser 6, the second-stage ejector 7, the second-stage condenser 8, and the third-stage ejector 9 and which used steam as an operating fluid, so that the vent gas from the distillation column 4 was condensed in the first-stage condenser 6 and the second-stage condenser 8. The condensate from the first-stage condenser 6 was recirculated in its entirety as a first-stage condensate to the distillation column 3. The condensate from the second-stage condenser 8 was recirculated in its entirety as a second-stage condensate to the acrylic acid absorbing column 2.

The mixed reaction gas (acrylic acid, 7.2 volume percent; water, 15.8 volume percent; inter gases including nitrogen, oxygen, etc., 76.6 volume percent; other components, 0.4 volume percent) from the reactor 1 was supplied to the acrylic acid absorbing column 2 at a flow rate of 22300 Nm$^3$/h. Water (containing 200 ppm hydroquinone as a polymerization inhibitor) as a solvent for use in absorbent was supplied to the acrylic acid absorbing column 2 at a flow rate of 2.2 m$^3$/h. Also, about 2 weight percent aqueous solution of acrylic acid recirculated as the second-stage condensate was supplied to the acrylic acid absorbing column 2 at a flow rate of 360 kg/h. Acrylic acid was absorbed in the acrylic acid absorbing column 2.

The bottom liquid (aqueous solution of acrylic acid) prepared in the acrylic acid absorbing column 2 was supplied to the distillation column 3. Also, about 30 weight percent aqueous solution of acrylic acid recirculated as the first-stage condensate was supplied to the distillation column 3 at a flow rate of 160 kg/h. In the distillation column 3, water was separated and discharged through the column top to carry out a rough distillation.

The liquid (crude acrylic acid) remaining on the bottom of the distillation column 3 was supplied to the distillation column 4 carry out a refinement therein. As a result, 5000 kg/h acrylic acid products (refined acrylic acid products) resulted. The acrylic acid products made up 96.7% of the total acrylic acid manufactured (refinement yield).

The operation was continued for one month, and the apparatus was opened for inspection. The weight of polymerized products was about 150 g in the acrylic acid absorbing column 2 and about 2 kg in the distillation column 3.

Comparative Example 1

The apparatus was operated under the same conditions as in the first embodiment, except that condensate was not recirculated at all from the vacuum generator. As a result, acrylic acid products were obtained at 4940 kg/h with a refinement yield of 95.6%.

The weight of polymers resulting from a one-month long, continuous operation was about 450 g in the acrylic acid absorbing column 2 and about 6 kg in the distillation column 3.

It would be understood from comparison of results of the first example and the first comparative example that the recirculation of condensed vent gas to the absorbing step and/or the refinement step according to the present invention improves the refinement yield of acrylic acid and reduces the weight of polymers manufactured.

EXAMPLE 2

The apparatus for manufacturing acrylic acid of FIG. 3 was used in place of the apparatus for manufacturing acrylic acid of FIG. 1 to carry out the process illustrated in FIG. 3 under the same conditions as in the first example to prepare acrylic acid products. Specifically, the apparatus was operated under the same conditions as in the first example, except that the condensate from the vacuum generator was not at all recirculated as in the first example and also that the vent gas from the atmospheric pressure distillation column 41 and the vent gas from the refined acrylic acid products storage vessel 43 were recirculated to the acrylic acid absorbing column 2 by the blower 42 as in FIG. 3. As a result, acrylic acid products were obtained at 4960 kg/h with a refinement yield of 96.0%.

The weight of polymers resulting from a one-month long, continuous operation was about 200 g in the acrylic acid absorbing column 2 and about 5 kg in the distillation column 3.

It would be understood from these results that the recirculation of the vent gas to the absorbing step and/or the refinement step according to the present invention improves the refinement yield of acrylic acid and reduces, even if the vent gas produced in the refinement step is recirculated without being condensed, the weight of polymers manufactured. The reduction in weight in such a case is substantial compared with a case that the acrylic acid contained in the vent gas is not recirculated, albeit not as significant as in the case that the vent gas is recirculated after being condensed. An apparatus for manufacturing acrylic acid used in this operation have an advantage in its relatively simple arrangement.

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

What is claimed is:

1. An apparatus for manufacturing (meth)acrylic acid for use in the method of manufacturing (meth)acrylic acid, the method comprising a reaction step, an absorbing step, and a refinement step, and further comprising a recirculation step of recirculating (meth)acrylic acid contained in a vent gas produced in the refinement step to the absorbing step and/or a later step, the apparatus comprising:

a reactor for carrying out a catalytic gas-phase oxidation reaction;

an absorbing column for absorbing (meth)acrylic acid from a (meth)acrylic-acid-containing mixed gas prepared in the reactor;

devices, disposed downstream of the absorbing column, for separating, refining, and recovering (meth)acrylic acid from a (meth)acrylic-acid-containing liquid prepared in the absorbing column; and paths for recirculating (meth)acrylic acid contained in a vent gas produced in the devices for separating, refining, and recovering (meth)acrylic acid from a (meth)acrylic-acid-containing liquid prepared in the absorbing column to the absorbing column and/or a device for separating and refining (meth)acrylic acid among the devices disposed downstream of the absorbing column.

2. An apparatus for manufacturing (meth)acrylic acid for use in the method of manufacturing (meth)acrylic acid, the method comprising a reaction step, an absorbing step, and a refinement step, and further comprising a recirculation step of recirculating (meth)acrylic acid contained in a vent gas produced in the refinement step to the absorbing step and/or a later step, the apparatus comprising:

a reactor for carrying out a catalytic gas-phase oxidation reaction;

an absorbing column for introducing a (meth)acrylic-acid-containing mixed gas prepared in the reactor and dissolving (meth)acrylic acid in a solvent so as to absorb the (meth)acrylic acid;

a solvent separation column for separating the solvent from a (meth)acrylic-acid-containing liquid prepared in the absorbing column to prepare a crude (meth)acrylic acid;

a fractionating column for fractionating the crude (meth)acrylic acid prepared in the solvent separation column;

a vacuum generator for maintaining the fractionating column in vacuum and condensing (meth)acrylic acid contained in a vent gas produced in the fractionating column; and a path for recirculating (meth)acrylic acid condensed in the vacuum generator to the absorbing column and/or the solvent separation column.

3. The apparatus for manufacturing (meth)acrylic acid as defined in claim 2, further comprising:

a path for recirculating a vent gas produced in the vacuum generator to the fractionating column without being treated.

4. The apparatus for manufacturing (meth)acrylic acid as defined in claim 2, further comprising:

a storage tank for recovering and storing fractionated (meth)acrylic acid; and a path for recirculating (meth)acrylic acid contained in a vent gas produced in the storage tank to at least one column selected from the absorbing column, the solvent separation column, and the fractionating column.

5. The apparatus for manufacturing (meth)acrylic acid as defined in claim 2, further comprising:

a storage tank for recovering and storing a condensate prepared in the vacuum generator; and a path for recirculating (meth)acrylic acid contained in a vent gas produced in the storage tank to at least one column selected from the absorbing column, the solvent separation column, and the fractionating column.

6. An apparatus for manufacturing (meth)acrylic acid for in the method of manufacturing (meth)acrylic acid, the method comprising a reaction step, an absorbing step, and a refinement step, and further comprising a recirculation step of recirculating (meth)acrylic acid contained in a vent gas produced in the refinement step to the absorbing step and/or a later step, the apparatus comprising:

a reactor for carrying out a catalytic gas-phase oxidation reaction;

an absorbing column for absorbing (meth)acrylic acid from a (meth)acrylic-acid-containing mixed gas prepared in the reactor;

a distillation column, disposed downstream of the absorbing column, for separating and refining (meth)acrylic acid from a (meth)acrylic-acid-containing liquid prepared in the absorbing column; and a path for recirculating a vent gas produced in the distillation column to the absorbing column disposed upstream of the distillation column.

7. The apparatus for manufacturing (meth)acrylic acid as defined in claim 6, further comprising:

a storage tank for recovering and storing refined (meth)acrylic acid; and a path for recirculating a vent gas produced in the storage tank to the absorbing column.

8. The apparatus for manufacturing (meth)acrylic acid as defined in claim 6, wherein the path includes a pressurizer for applying a pressure to the vent gas produced in the distillation column.

9. An apparatus for manufacturing (meth)acrylic acid for use in the method of manufacturing (meth)acrylic acid, the method comprising a reaction step, an absorbing step, and a refinement step, and further comprising a recirculation step of recirculating (meth)acrylic acid contained in a vent gas produced in the refinement step to the absorbing step and/or a later step, the apparatus comprising:

a reactor for carrying out a catalytic gas-phase oxidation reaction;

a first absorbing column for absorbing (meth)acrylic acid from a (meth)acrylic-acid-containing mixed gas prepared in the reactor;

a distillation column, disposed downstream of the absorbing column, for separating and refining (meth)acrylic acid from a (meth)acrylic-acid-containing liquid prepared in the absorbing column;

a second absorbing column disposed downstream of the distillation tower, for absorbing (meth)acrylic acid from a vent gas produced in the distillation column; and a path for recirculating the (meth) acrylic acid absorbed by the second absorbing column to the first absorbing column and/or the distillation column.

10. The apparatus for manufacturing (meth)acrylic acid as defined in claim 9, further comprising:

a storage tank for recovering and storing refined (meth)acrylic acid; and a path for recirculating (meth)acrylic acid contained in a vent gas produced in the storage tank through the second absorbing column to the first absorbing column and/or the distillation column.

* * * * *